United States Patent
Moser et al.

(10) Patent No.: US 10,086,399 B2
(45) Date of Patent: Oct. 2, 2018

(54) DEVICE FOR ADMINISTERING A FLUID PRODUCT

(71) Applicant: Faulhaber Precistep SA, La Chaux-de-Fonds (CH)

(72) Inventors: Yves Moser, La Chaux-de-Fonds (CH); Jonas Monnin, La Ferriere (CH)

(73) Assignee: Faulhaber Precistep SA (CH)

( * ) Notice: Subject to any disclaimer, the term of this patent is extended or adjusted under 35 U.S.C. 154(b) by 0 days.

(21) Appl. No.: 15/115,571

(22) PCT Filed: Mar. 21, 2014

(86) PCT No.: PCT/EP2014/055737
§ 371 (c)(1),
(2) Date: Jul. 29, 2016

(87) PCT Pub. No.: WO2015/139775
PCT Pub. Date: Sep. 24, 2015

(65) Prior Publication Data
US 2016/0368018 A1    Dec. 22, 2016

(51) Int. Cl.
*B05C 17/005* (2006.01)
*A61M 5/315* (2006.01)
(Continued)

(52) U.S. Cl.
CPC ... *B05C 17/00576* (2013.01); *A61M 5/31511* (2013.01); *A61M 5/31513* (2013.01);
(Continued)

(58) Field of Classification Search
CPC ........... A61M 5/31511–5/31515; B05B 11/02; B05C 17/005; B05C 17/00576;
(Continued)

(56) References Cited

U.S. PATENT DOCUMENTS 3,793,498 A * 2/1974 Matsui ............... H01H 35/14
180/274
4,298,575 A * 11/1981 Berglund ............ B01L 3/0227
222/309
(Continued)

FOREIGN PATENT DOCUMENTS

DE    102010012067 A1    3/2011
EP        1897575 A2    3/2008
WO    WO-00/59643 A1    10/2000

OTHER PUBLICATIONS

International Search Report and Written Opinion of PCT/EP2014/055737, dated May 8, 2014, 4 pages.

*Primary Examiner* — Nicholas J Weiss
*Assistant Examiner* — Bob Zadeh
(74) *Attorney, Agent, or Firm* — Blank Rome LLP

(57) ABSTRACT

A device for administering a fluid product, such as an industrial or a medical compound. The device includes a reservoir (18) in which a plunger (15) is axially movable, and an axially movable rod (16) on which a ferromagnetic rod connector (12) is attached. The ferromagnetic rod connector (12) is adapted for sliding cooperation within the reservoir (18). And, a detachable mechanical connection is provided between the plunger (15) and the ferromagnetic rod connector (12). A ferromagnetic plunger connector (13) is attached to the plunger and a magnet (11), arranged for magnetic cooperation with the ferromagnetic connectors (12, 13), to provide a mechanical connection between the ferromagnetic connectors.

15 Claims, 4 Drawing Sheets

(51) Int. Cl.
*B05C 5/02* (2006.01)
*G01F 11/02* (2006.01)
*B23K 3/06* (2006.01)
*B65D 83/00* (2006.01)
*B05B 11/02* (2006.01)
*H05K 3/34* (2006.01)

(52) U.S. Cl.
CPC ........... *A61M 5/31515* (2013.01); *B05C 5/02* (2013.01); *B05C 17/005* (2013.01); *B23K 3/0638* (2013.01); *B65D 83/0033* (2013.01); *G01F 11/021* (2013.01); *B05B 11/02* (2013.01); *H05K 3/3484* (2013.01)

(58) Field of Classification Search
CPC .... B05C 5/02; B23K 3/0638; B65D 83/0033; G01F 11/021; H05K 3/3484
See application file for complete search history.

(56) References Cited

U.S. PATENT DOCUMENTS

| | | | |
|---|---|---|---|
| 4,677,980 A * | 7/1987 | Reilly | A61M 5/007 128/DIG. 1 |
| 4,848,606 A | 7/1989 | Taguchi et al. | |
| 5,334,353 A * | 8/1994 | Blattner | B01L 3/0241 141/130 |
| 5,348,585 A | 9/1994 | Weston | |
| 5,375,738 A * | 12/1994 | Walsh | B05C 5/001 222/1 |
| RE35,979 E * | 12/1998 | Reilly | A61M 5/007 128/DIG. 1 |
| 6,752,789 B2 * | 6/2004 | Duchon | A61M 5/14216 604/218 |
| 7,491,191 B2 * | 2/2009 | Wagner | A61M 5/007 604/228 |
| 8,066,629 B2 * | 11/2011 | Dlugos | A61F 5/0003 600/37 |
| 9,114,215 B2 * | 8/2015 | Cowan | A61M 5/31513 |
| 9,533,093 B2 * | 1/2017 | Schafer | A61M 5/1452 |
| 2002/0022807 A1 * | 2/2002 | Duchon | A61M 5/14216 604/228 |
| 2005/0015056 A1 * | 1/2005 | Duchon | A61M 5/14216 604/218 |
| 2011/0152785 A1 * | 6/2011 | Chattaraj | A61M 5/31511 604/222 |
| 2011/0301566 A1 | 12/2011 | Schaefer | |
| 2016/0368018 A1 * | 12/2016 | Moser | A61M 5/31511 |

\* cited by examiner

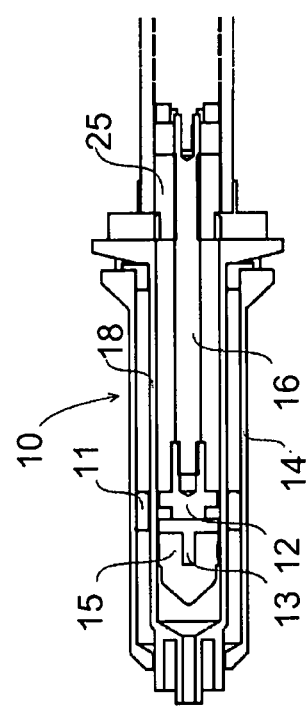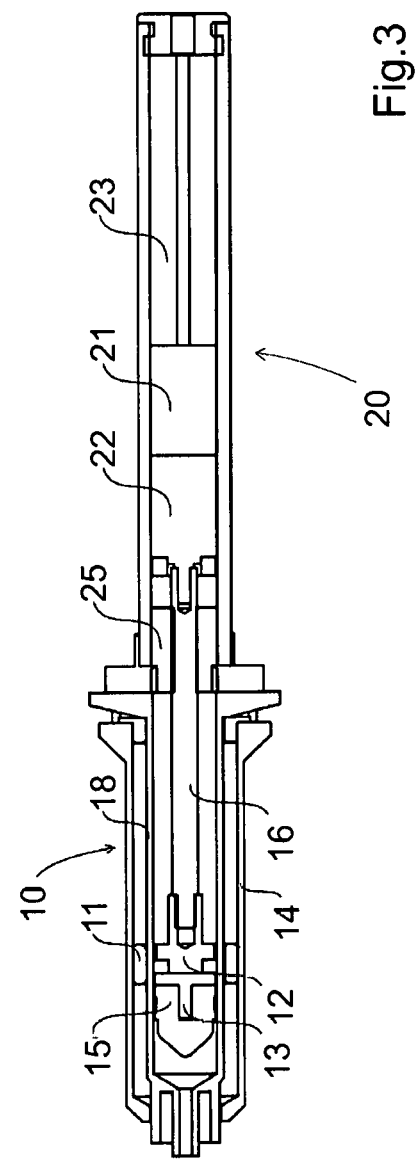

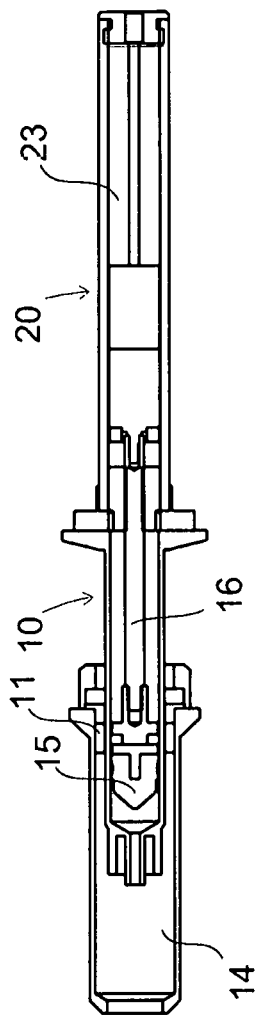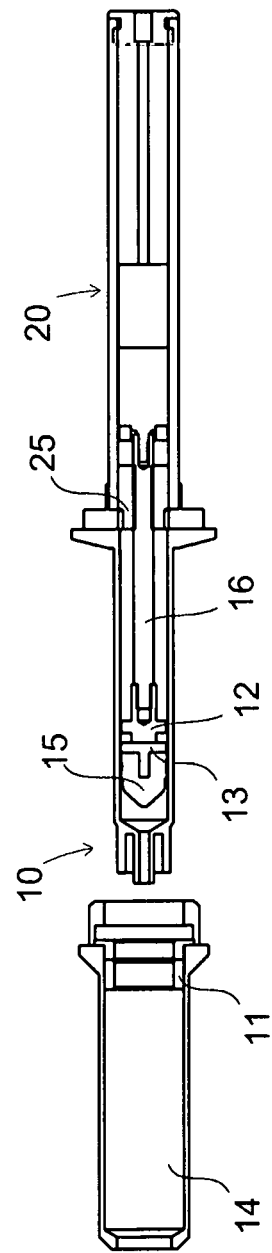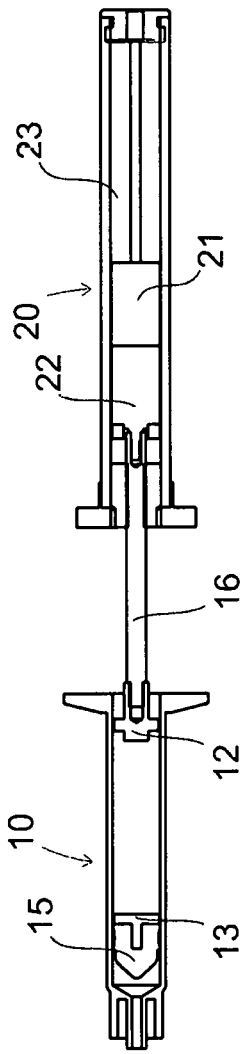

DEVICE FOR ADMINISTERING A FLUID PRODUCT

RELATED APPLICATIONS

This application is a national phase of PCT/EP2014/055737, filed on Mar. 21, 2014. The content of the application is hereby incorporated by reference.

FIELD OF THE INVENTION

The present invention relates to a device for administering a fluid product, primarily in industrial field to dispense fluids such as glue, lubricant, solder paste, liquids, etc., but also for dispensing drugs. It is also related to a motorized high precision volumetric liquid dispensing device.

DESCRIPTION OF RELATED ART

Deposition of controlled amounts of fluid, such as liquids, in industrial applications is a very challenging issue. Many applications require a very precise amount of fluid to be dispensed.

One prior art solution to this problem is to provide an applicator having a reservoir of fluid and an actuator to drive a plunger in the reservoir in order to extrude the fluid.

Also known in the art is the use of peristaltic pumps that continuously introduce a fluid into an intravenous tube. These devices usually employ a gravity-fed tube attached to a reservoir (usually an intravenous bag or bottle) and a motor-driven pump that regulates the flow of fluid via a cam that alternately compresses and releases the tube. This technology lacks the industrial precision requirements.

More pertinent to the industrial context are pneumatic pressure-driven fluid dispensers, which have a syringe containing the fluid to be dispensed attached to a controller that also controls a compressed air supply (usually "shop air"). Fluid is dispensed when the controller introduces compressed air into the syringe that depresses the syringe piston over a specific distance. A disadvantage of this technology is the variability in the amount dispensed during successive operations of the syringe as the fluid is depleted in the syringe.

U.S. Pat. No. 4,848,606 shows an apparatus for dispensing a predetermined volume of paste-like fluid that has a motor attached to one end of a threaded screw rod and a nozzle holder functionally connected to the screw rod. To control the Z-axis position of the nozzle, the motor is operated, thereby rotating the screw rod and causing the nozzle holder to travel up and down the rod threads. The dispensing is accomplished by a second motor and screw rod combination, this time having a piston-driving device coupled to a piston that is disposed within the nozzle. Operation of the second motor rotates the second screw rod, causing axial movement of the piston and subsequent fluid dispensing from the nozzle. One drawback of the device is that it uses an indirect mechanical coupling between the rotating motor and the piston or plunger.

Another major drawback of all these dispensers is that the volume of fluid to be extruded cannot be controlled as precisely as desired.

Another limitation of those prior art devices, especially dispensers of higher viscosity fluids, is that there is a residual dispensing, leakage or oozing of the fluid after the driving mechanism has stopped, slowly expelling extra, unwanted fluid. The dispensing apparatus cannot be moved to the next location since the leaking fluid would be dripped onto unwanted areas as the dispenser moves to the new location. A significant amount of time is sometimes required before moving without any leaking. This limitation prevents accuracy, precision and time efficient operation of the dispensing apparatus in several industrial applications.

In order to prevent this risk of fluid leakage, it is known to retract the plunger by a short distance after the fluid dispense, in order to draw back the leaking droplet into the reservoir. This requires however a fix connection between the plunger and the driving rod, in order to push or pull the plunger in both directions. Such a fix connection is often difficult to disconnect, making the replacement of the syringe difficult or time consuming.

U.S. Pat. No. 5,348,585 discloses a motor driven dispenser with a rotating drive rod mechanically interconnected with a piston in a cartridge. Apparently from the patent, the piston rotates within the cartridge which makes the sealing between piston and cartridge problematic.

WO00/59643 describes an approach to dispense precise amount of fluids with a relatively large range of viscosities. This method uses a threaded plunger to make the connection with the moving rod. Therefore, this system requires having a rod which is not rotating when moving axially and therefore a sliding leadscrew which is driven through a hollow motor. Such an arrangement requires oversizing the motor in order to have enough torque to move viscous fluid; a gearhead is not possible. This results in a heavy system not easy to handle. Moreover, the precision of the liquid dispensed is limited by the motor precision and cannot be increase by the use of a gearhead. Another drawback of this method is that a small force is required for connecting and disconnecting the plunger from the system. This often results in unwanted liquid ejection or introduction of air bubbles in the syringe.

EP1897575A2 describes a motorized injection device with a magnetic locking system between the syringe plunger and the actuating shaft. The syringe plunger includes a permanent magnet while the actuating shaft includes a ferrous metal. During the connecting procedure, the actuating shaft is driven forward to contact the syringe plunger, and the syringe plunger remains magnetically attached to the actuating shaft. One of the benefits of utilizing a magnetic syringe plunger arrangement is that a "zero" engagement force is required. Such an approach is also compatible with a rotating rod. To release the connection, a plate is located proximal to the syringe body, and the plate defines an aperture for allowing manipulation of the syringe plunger. The syringe plunger further includes a base having an outer diameter larger than the aperture of the plate. During the disconnecting procedure, the syringe plunger is retracted until the base abuts against an inner surface of the plate. This solution requires modified syringes with a release plate strong enough to resist the magnetic attraction force. Moreover, it is almost not possible to disconnect the plunger from the shaft without displacing the plunger inside the syringe. This is a drawback if the syringe needs to be reused, since the volume of liquid within the syringe and the amount of displacement needed to expel a desired volume of liquid will be lost.

None of the above described devices is really satisfactory as they require a medium connecting axial force and a large disconnecting axial force. This results in unwanted displacement of the plunger inside the syringe when replacing the later. This also often results in unwanted liquid ejection or introduction of air bubbles in the syringe. Some devices request a destructive disconnection.

Therefore, a first aim of the present invention is to provide a fluid product-dispensing device avoiding the above-mentioned limitations.

In particular, an aim is to provide a volumetric dispensing device for repetitively dispensing a precise amount of fluid.

Another aim of the invention is to provide a light and compact volumetric dispenser with a high dispensing force.

A further aim of the invention is to provide a fluid dispenser allowing easy connection and disconnection between the plunger and the actuating module.

A further aim of the invention is to provide a fluid dispenser allowing a non destructive disconnection between the plunger and the actuating module.

A further aim of the invention is to provide a fluid dispenser allowing disconnection between the plunger and the actuating module without moving the plunger inside the syringe.

A further aim of the invention is to provide a fluid dispenser with a rotating shaft actuated by a rotating motor, and a non rotating plunger.

A further aim of the invention is to provide a fluid dispenser with a rotating shaft actuated by a rotating motor, thus allowing a reduction gear between the motor and the shaft.

A still further aim of the invention is to provide a fluid dispenser that is easy to integrate into an assembly line workstation.

Another object of the present invention is to provide a means for repetitively dispensing a precise and optimum amount of fluid.

A further object of the present invention is to provide a fluid dispensing means having sufficient rigidity, durability, and light weight to meet production line requirements.

BRIEF SUMMARY OF THE INVENTION

According to the invention, these aims are achieved by means of a device for administering a fluid product comprising:
  a reservoir;
  a plunger axially movable within said reservoir, said plunger comprising a ferromagnetic plunger connector;
  an axially movable rod comprising a ferromagnetic rod connector;
  a magnet, arranged for magnetic cooperation with said ferromagnetic connectors to provide a magnetic connection between the plunger connector and the rod connector.

Such an arrangement provides a magnetic connection between the plunger and the axially movable rod, using a ferromagnetic connector attached to the plunger/piston and a counter-ferromagnetic connector attached to the rod. Both connectors establish a magnetic circuit with the magnet. This magnetic circuit can be easily closed by moving the magnet in the vicinity to the connectors in order to connect the rod with the plunger. The magnetic circuit can also be easily open by removing the magnet away from both ferromagnetic connectors, thus interrupting the magnetic attraction between plunger and rod and between both connectors and magnet.

The reservoir could be cylindrical.

The device further allows having a strong axial force while still allowing the plunger to slide without rotating inside the reservoir even when using a rotating rod connector.

Furthermore, this arrangement allows having a rigid axial connection between the rod and the plunger. When the rod and the plunger are mutually connected with the magnet, the plunger can be pushed in one direction and pulled in the reverse direction by the rod.

The rod and the plunger can be disconnected by moving the magnet and breaking the magnetic circuit, without displacing the plunger. When the rod and the plunger are disconnected, the rod can be removed outside of the reservoir without moving the plunger.

In an embodiment, the magnet is provided outside of the reservoir.

In an embodiment, the magnet has an annular profile with an inner diameter substantially corresponding to the outer diameter of the reservoir.

In such configuration, an external magnet enables a mechanical connection between the two ferromagnetic connectors due to a magnetic field induced by the outer magnet.

Advantageously, the magnet is slidably movable along the reservoir. In this way, the external magnet can follow the connectors during axial displacement of the plunger.

In a variant, the magnet is removable from the reservoir, and can be reused even if the reservoir is disposable.

In a preferred embodiment, the rod connector has an extending head with reduced diameter. Such geometry allows reducing the torque transmitted between the connectors. Such geometry further concentrates the magnetic field within a smaller section.

The rod connector is advantageously attached to or integral with a threaded rod.

The rod connector and the rod can be rotated by the motor.

The threaded rod can be mounted into a fixed nut provided on the actuating module, so that rotation of the rod causes a linear displacement of the rod and rod connector.

In a further variant, the threaded rod is rotated by an actuator module provided with a rotating stepper motor and a gear head. Such a gear head increases the torque transmitted to the rod and increases the precision, while simultaneously reducing the weight of the motor.

The stepper motor and gear head are preferably slidably mounted into an inner volume of the actuating module, following the piston motion.

In an advantageous embodiment, said device for administering a product is a syringe adapted for administering a medical compound.

The invention further provides a process for administering a fluid product, using a reservoir in which a plunger with a ferromagnetic plunger connector is axially movable, comprising the steps of:
  providing an axially movable rod on which a ferromagnetic rod connector is attached;
  inserting said movable rod into said reservoir, until said rod connector is in contact with said plunger connector;
  placing at least one magnet into magnetic cooperation with the rod connector and with the plunger connector in order to provide a magnetic field connecting both connectors together;
  using an actuating module to displace the plunger and thereby administrate said fluid;
  removing said magnet from magnetic cooperation with said connectors;
  disconnecting the two connectors from mutual cooperation;
  removing the rod and rod connector from the administering device.

BRIEF DESCRIPTION OF THE DRAWINGS

The invention will be better understood with the aid of the description of an embodiment given by way of example and illustrated by the figures, in which:

FIG. 2 is a close view of the administering module with the outer tube of the magnetic locking mechanism attached on the volumetric dispenser;

FIG. 3 is a complete view of an example of a volumetric dispenser according to the invention;

FIGS. 4a to 4g illustrate the various steps to install and remove an administering module with an automatic motorized actuating module.

DETAILED DESCRIPTION OF POSSIBLE EMBODIMENTS OF THE INVENTION

Figure 1:
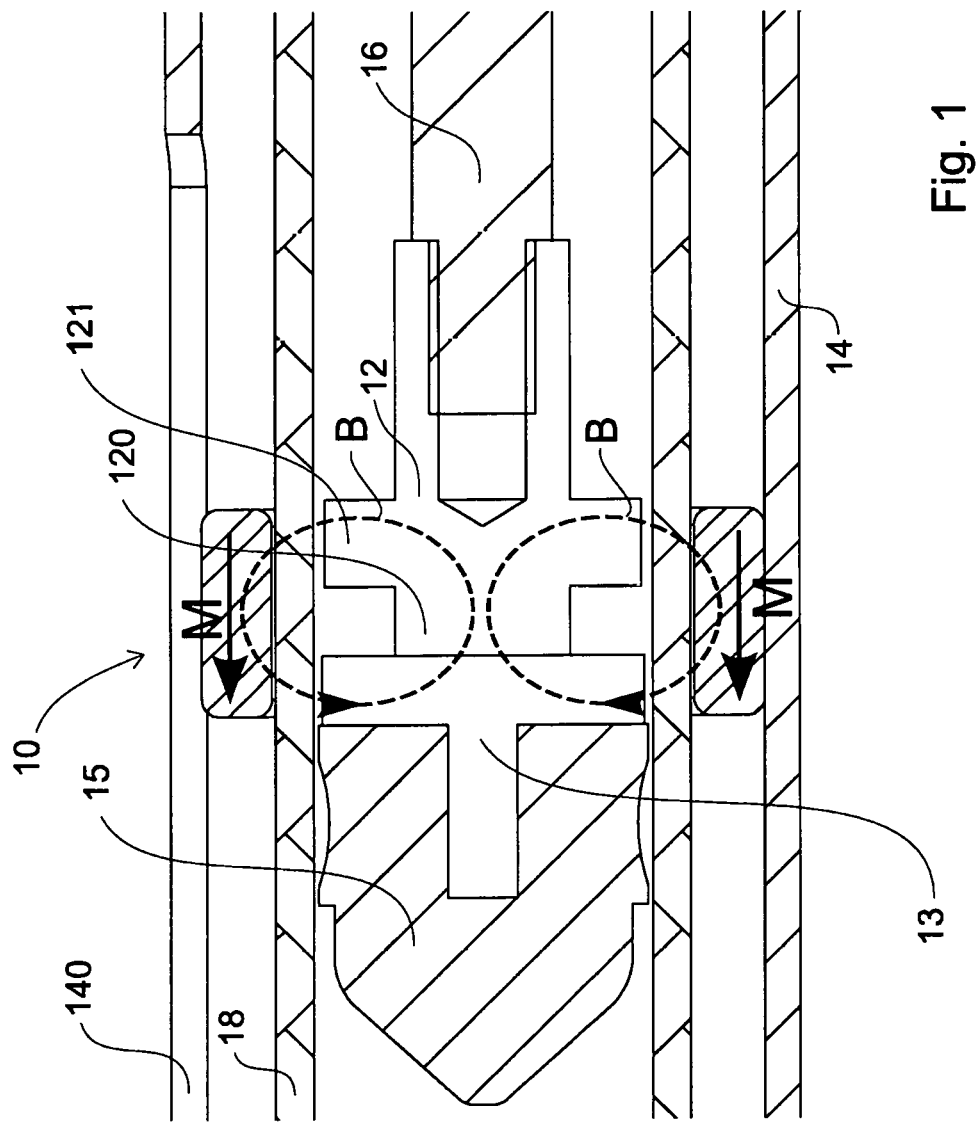
FIG. 1 is a schematic representation of a magnetic locking system for use with an administering module.

FIG. 1 shows a schematic representation of an example of an administering module 10 with a magnetic locking system according to the invention. Such a system is advantageously used in industry to deliver small quantities of fluids, such as liquids or compounds, in technical uses where the deliveries shall be provided in well controlled conditions, with respect to quantities, time intervals, delivery rate, contamination free ambiances, etc.

The administering module comprises a plunger 15 (or piston) slidably movable within a cylindrical reservoir 18. The plunger can be made of synthetic material for example, or of metal with a synthetic seal between plunger and the inner side of the reservoir. A ferromagnetic plunger connector 13 is attached to or integral with the plunger 15.

The module 10 further comprises a threaded rod (or shaft) 16 that can be moved axially and in rotation by an actuating module 20. The distal end of the rod is provided with a ferromagnetic rod connector 12 for connecting the rod with the plunger. The rod 16 can be used to push and pull the plunger 15 within the reservoir 18 in order to expel a liquid outside of the reservoir 18, respectively to draw liquid into the reservoir, when the connectors 12 and 13 are mutually connected.

A magnet 11 outside of the reservoir 18 is in magnetic cooperation with both ferromagnetic connectors 12 and 13. In one preferred embodiment, the magnet comprises at least one permanent magnet. Alternatively, the magnet can comprise one inductive coil for generating a magnetic field when a current passes through the coil.

The magnets and connectors are arranged in such a way that a magnetic circuit can be established between the magnet 11 and the two connectors 12, 13, and between the two connectors. The magnetic field is oriented so that the two opposite connectors are attracting each other. In FIG. 1, the resulting magnetic field B is illustrated with the two dotted lines arrows.

In a preferred embodiment, as illustrated in FIG. 1, the magnetic field is optimized with an interfacing zone 120 that has a reduced diameter compared to the diameter of adjacent connectors. In the example of FIG. 1, the rod connector 12 comprises two longitudinal sections with two different diameters: a first proximal section 121 with a large diameter in order to reduce the gap between this section 121 and the magnet 11, and a distal section 120 (or head) with a smaller diameter that concentrates the magnetic field. This architecture allows increasing the axial force between the two connectors while reducing the torque transmitted by the rod 16 to the plunger 15 when the rod rotates.

FIG. 2 and FIG. 3 are more complete representations of an example of embodiment of a device for administering a substantially liquid product in accordance with the invention.

The above described connectors 12 and 13, together with the cooperating magnet 11 are used in order to provide a detachable mechanical connection between an actuating module 20 and an administering module 10 provided with a cylindrical reservoir 18. Such a connection is required when the actuating module is used to displace the plunger 15 of the administering module in both directions within the reservoir 18.

When the administering module needs to be disposed or cleaned or controlled, it is quickly and easily disconnected from the actuating device, simply by removal of the magnet 11 from magnetic cooperation with the two connectors 12, 13, thereby immediately interrupting the magnetic circuit. The two connectors are then free to be separated from each other, and the administering module may be removed.

In the illustrated embodiment, a single annular magnet 11 is provided inside an optional outer tube, hereinafter called outer-tube 14. A magnet with a different shape could also be considered. The magnet 11 is slidably movable within the outer-tube 14 and along the reservoir 14. The magnet is guided by the outer-tube. The outer-tube can comprise one or more windows, such as elongated holes, in its sides in order to view the position of the magnet and of the plunger, and for displacing the plunger relative to the reservoir.

The over-tube 14 could be screwed or otherwise mounted to the actuating module 20.

A motor, such as for instance a rotating stepper motor 21, is used to rotate the rod 16 that extends from the actuating module 20 into the reservoir 18. The rod length is adapted to enable it to enter into the inner tube of an administering module axially aligned with the actuating module.

A gear head 22 is advantageously provided between the motor 21 and the rod 16. The gear head increases the torque transmitted to the rod 16 by a given motor 21, and increases the precision of the displacement of the plunger. It also enables the use of a small stepper motor 21, thus reducing the weight of the assembly.

In the illustrated embodiment, the threaded rod 16 is engaged within the nut 25 which is fixed relative to the over-tube 14 and to the actuating module 20. Therefore, the rod 16 is axially moved when it is rotated by the motor 21. The motor and rod assembly may then drive the plunger 15 in order to deliver the required product in the required conditions.

As seen in the figures, the gear head and stepper motor can slide inside an inner volume 23 of the actuating module 20, following the plunger motion.

The various steps to connect and disconnect an administering module 10 to an actuating module 20 will now be described in relation with FIGS. 4a to 4g.

Figure 4A:
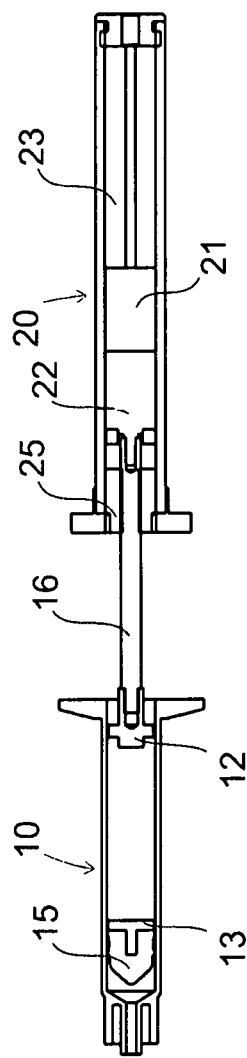

The first step consists in placing the administering module 10 into axial alignment with a corresponding actuating module 20, as shown in FIG. 4a.

Figure 4B:
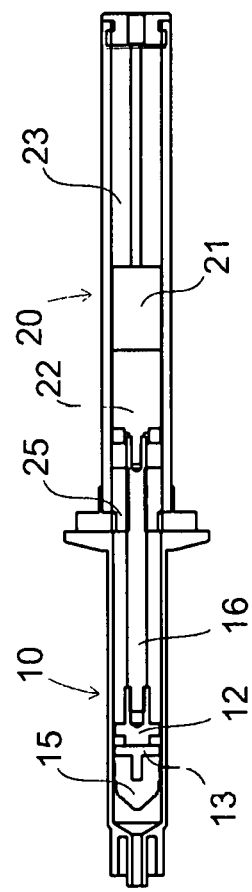

During this operation, the two ferromagnetic connectors, that is to say the rod-connector 12 and the plunger connector 13, enter in contact without force, as shown in FIG. 4b.

Figure 4C:
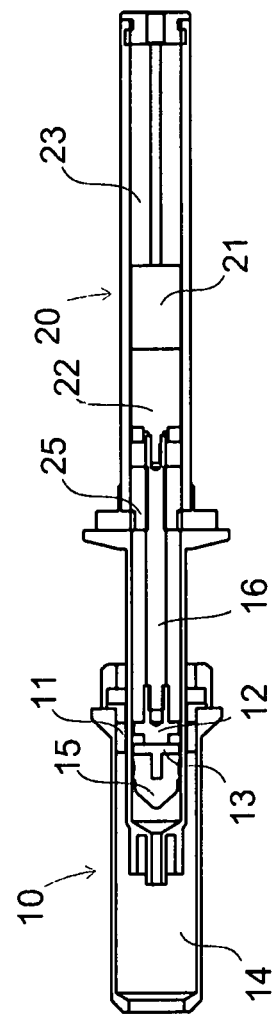

The next step consists in placing an over-tube 14 with the magnet 11 around the reservoir 18, as shown in FIG. 4c.

The magnet 11 within the over-tube 14 can be slided around the reservoir 18 at the axial position corresponding to those of the two connectors 12, 13.

In another embodiment, a magnet 11 is placed outside of the reservoir 18, and guided with other guiding means, without any over-tube.

In this position, the permanent magnet 11 generates a magnetic field B involving the two adjacent ferromagnetic connectors 12 and 13, so that a magnetic field B is established as shown in FIG. 1 by the two rotating arrows, representing the magnetic field.

Figure 4D:
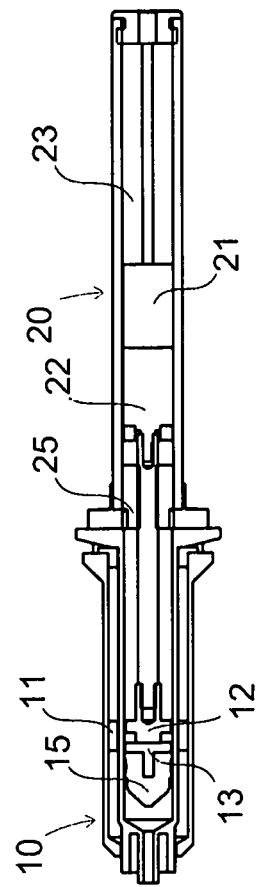

FIG. 4d illustrates the next step in which the administering module 10 is connected to the actuating module 20, in this example by screwing the over-tube 14 to the actuating module 20.

The annular magnet 11 provides a strong magnetic connection between the two connectors 12 and 13. The over-tube 14 provides a guide into which the magnet 11 is slidably mounted. At least one window through a side wall of the over-tube 14 is provided in order to see the position of the plunger within the cylinder, or to move the magnet 11 if needed.

Such an arrangement enables the actuating module 20 to displace the rod 16 and therefore the plunger 15 in both directions.

The reduced contacting surface of the head 120 of the rod connector 12 limits the torque transmitted to the plunger connector 13 when the rod 16 and rod connector are in rotation. Therefore, the plunger connector 13 and plunger 15 do not rotate even if the rod connector 12 rotates with the shaft.

FIGS. 4e and 4f illustrates the following step, in which the over-tube is unscrewed and removed, thus enabling the removal of the over-tube from the administering module 10.

As the annular permanent magnet 11 is locked inside the over-tube 14, by removing the later, the permanent magnet 11 is taken away. During this step, the force applied on the plunger by displacement of the magnet is lower than the force needed to displace the plunger inside the reservoir. Such a low force is not sufficient to cause a displacement of the plunger.

Many variants of the present invention may be provided, without departing from the spirit and scope of the invention.

For instance, in a variant, the outer tube 14 is replaced by a plurality of longitudinal rails cooperating with the magnet 11, and acting as a guide for guiding the axial displacement of the latter along the cylinder 18.

In another variant, the stepper motor, rotating threaded rod and screw arrangement are replaced by a linear motor. In such an arrangement, the actuating rod does not require to be threaded.

In a further embodiment, the administering module is a syringe, and the product to be delivered is a medical compound. In such an embodiment, the syringe is provided to be easily and quickly connectable/removable from the actuating device, for instance to replace the syringe between two medical treatments or the like. For such uses, the syringes are advantageously disposable. For such an embodiment, the previous description in relation with FIGS. 1 to 4 is also applicable, considering that the administering module is a syringe. As commonly used in this field, the syringe is preferably provided with a detachable needle or other adequate adaptor suitable for injection into the skin.

The invention claimed is:

1. A device for administering a fluid product comprising:
   a reservoir;
   a plunger axially movable within said reservoir, said plunger comprising a ferromagnetic plunger connector;
   an axially movable rod comprising a ferromagnetic rod connector;
   a magnet, arranged for magnetic cooperation with said ferromagnetic plunger connector and with said ferromagnetic rod connector, to provide a magnetic connection between the ferromagnetic plunger connector and the ferromagnetic rod connector, wherein said magnet is provided outside the reservoir and is slidably movable along the reservoir.

2. A device according to claim 1, further comprising a guide element for guiding a displacement of said magnet along the reservoir.

3. A device according to claim 2, comprising a tube around said reservoir, said tube acting as said guide element.

4. A device according to claim 1, wherein said ferromagnetic plunger connector, said ferromagnetic rod connector and said magnet together establish a magnetic circuit, wherein said circuit can be interrupted by sliding said magnet along said reservoir in order to disconnect the ferromagnetic plunger connector and the ferromagnetic rod connector.

5. A device according to claim 1, wherein said magnet comprises a permanent magnet.

6. A device according to claim 1, wherein said magnet comprises a coil.

7. A device according to claim 1, wherein said magnet is removable from said device.

8. A device according to claim 1, wherein said rod is rotatable relative to said reservoir and to said plunger.

9. A device according to claim 1, wherein said ferromagnetic rod connector is provided with an extending head with reduced diameter.

10. A device according to claim 1, wherein the ferromagnetic rod connector is attached to said axially movable rod rotatably mounted into a fixed nut.

11. A device according to claim 1, further comprising an actuating module provided with a rotating stepper motor and a gear head.

12. A device according to claim 1, wherein the fluid product comprises a glue, a lubricant, and/or a solder paste.

13. A device according to claim 1, wherein the fluid product comprises a medical compound.

14. A process for administering a fluid product using an administering device having a reservoir in which a plunger with a ferromagnetic plunger connector is axially movable, comprising the steps of:
   providing an axially movable rod on which a ferromagnetic rod connector is attached;
   inserting said movable rod into said reservoir, until said ferromagnetic rod connector is in contact with said ferromagnetic plunger connector;
   placing at least one magnet, which is located outside the reservoir and is arranged so that it is slidably movable along the outside of the reservoir, into magnetic cooperation with the ferromagnetic rod connector and with the ferromagnetic plunger connector in order to provide a magnetic field connecting the ferromagnetic rod connector and the ferromagnetic plunger connector together;
   using an actuating module to displace the plunger and thereby administrate said fluid product;
   removing said magnet from magnetic cooperation with the ferromagnetic rod connector and ferromagnetic plunger connector;
   disconnecting the ferromagnetic rod connector and ferromagnetic plunger connector from mutual cooperation;
   removing the moveable rod and the ferromagnetic rod connector from the administering device.

15. The process of claim 14, wherein the fluid product is a medical compound and the administering device is a syringe.

* * * * *